(12) United States Patent
Vincent et al.

(10) Patent No.: US 9,744,530 B2
(45) Date of Patent: Aug. 29, 2017

(54) TREATMENT OF AROMATIC ALKYLATION CATALYSTS

(71) Applicant: EXXONMOBIL CHEMICAL COMPANY, Baytown, TX (US)

(72) Inventors: Matthew J. Vincent, Kingwood, TX (US); Terry E. Helton, Montgomery, TX (US); Dominick A. Zurlo, Easton, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 28 days.

(21) Appl. No.: 14/781,781

(22) PCT Filed: Apr. 22, 2014

(86) PCT No.: PCT/US2014/034973
§ 371 (c)(1),
(2) Date: Oct. 1, 2015

(87) PCT Pub. No.: WO2014/182434
PCT Pub. Date: Nov. 13, 2014

(65) Prior Publication Data
US 2016/0038928 A1 Feb. 11, 2016

Related U.S. Application Data

(60) Provisional application No. 61/821,587, filed on May 9, 2013.

(30) Foreign Application Priority Data

Jul. 22, 2013 (EP) .................................... 13177334

(51) Int. Cl.
*C07C 2/66* (2006.01)
*B01J 37/08* (2006.01)
*B01J 38/48* (2006.01)
*B01J 29/70* (2006.01)
*B01J 29/08* (2006.01)
*B01J 37/06* (2006.01)

(52) U.S. Cl.
CPC ............. *B01J 37/08* (2013.01); *B01J 29/084* (2013.01); *B01J 29/70* (2013.01); *B01J 29/7007* (2013.01); *B01J 29/7038* (2013.01); *B01J 37/06* (2013.01); *B01J 38/48* (2013.01); *C07C 2/66* (2013.01); *C07C 2521/04* (2013.01); *C07C 2529/08* (2013.01); *C07C 2529/70* (2013.01); *Y02P 20/52* (2015.11); *Y02P 20/584* (2015.11)

(58) Field of Classification Search
CPC ....... C07C 2/66; C07C 15/073; C07C 15/085; C07C 2521/04; C07C 2529/08; C07C 2529/70; B01J 29/084; B01J 29/70; B01J 29/7038; B01J 37/06; B01J 37/08; B01J 38/48
USPC ....................................... 502/64, 61, 63, 202
See application file for complete search history.

(56) References Cited

U.S. PATENT DOCUMENTS

| | | |
|---|---|---|
| 3,751,504 A | 8/1973 | Keown et al. |
| 4,016,218 A | 4/1977 | Haag et al. |
| 4,429,176 A | 1/1984 | Chester et al. |
| 4,522,929 A | 6/1985 | Chester et al. |
| 4,547,605 A | 10/1985 | Kresge et al. |
| 4,594,146 A | 6/1986 | Chester et al. |
| 4,663,492 A | 5/1987 | Chester et al. |
| 4,891,458 A | 1/1990 | Innes et al. |
| 4,992,606 A | 2/1991 | Kushnerick et al. |
| 5,077,445 A | 12/1991 | Le |
| 5,258,565 A | 11/1993 | Kresge et al. |
| 5,334,795 A | 8/1994 | Chu et al. |
| 5,371,310 A | 12/1994 | Bennett et al. |
| 5,453,554 A | 9/1995 | Cheng et al. |
| 8,222,468 B2 | 7/2012 | Clark et al. |

FOREIGN PATENT DOCUMENTS

| | | |
|---|---|---|
| WO | 2008/098676 | 8/2008 |
| WO | 2010/082963 | 7/2010 |

*Primary Examiner* — Sharon Pregler
(74) *Attorney, Agent, or Firm* — Darryl M. Tyus

(57) ABSTRACT

The present disclosure relates to a method for treating a catalyst that is useful for producing mono-alkylaromatic compounds, the method comprises the steps of (a) contacting the untreated catalyst with water to produce water-contacted catalyst, and (b) drying the water-contacted catalyst with a drying gas without steam being formed at a temperature of less than 300° C. to produce a treated catalyst. The treatment is effective to improve the activity and catalyst selectivity. A process for producing a mono-alkylaromatic compound comprising such a catalyst treatment is also disclosed.

23 Claims, 2 Drawing Sheets

TREATMENT OF AROMATIC ALKYLATION CATALYSTS

CROSS REFERENCE TO RELATED APPLICATIONS

This application is a National Stage Application of International Application No. PCT/US2014/034973, filed Apr. 22, 2014, and claims the benefits of U.S. Provisional Application Ser. No. 61/821,587 filed May 9, 2013, and priority to EP 13177334.3 filed Jul. 22, 2013, which are incorporated by reference in their entireties.

FIELD OF THE INVENTION

The present invention relates to a method of treating a catalyst, preferably an alkylation or transalkylation catalyst, and an alkylation or transalkylation process for production of mono-alkylaromatic compounds using the treated catalyst.

BACKGROUND OF THE INVENTION

Mono-alkylaromatic compounds, such as ethylbenzene and cumene are valuable commodity chemicals which are used industrially for the production of styrene monomer and phenol respectively. Ethylbenzene may be produced by a number of different chemical processes, but one process which has achieved a significant degree of commercial success is the vapor phase alkylation of benzene with ethylene in the presence of a solid, acidic ZSM-5 zeolite catalyst. In the commercial operation of this process, the polyalkylated benzenes, including both polymethylated and polyethylated benzenes, which are inherently co-produced with ethylbenzene in the alkylation reactor, are transalkylated with benzene to produce additional ethylbenzene either by being recycled to the alkylation reactor or by being fed to a separate transalkylation reactor. Examples of such ethylbenzene production processes are described in U.S. Pat. No. 3,751,504 (Keown), U.S. Pat. No. 4,547,605 (Kresge), and U.S. Pat. No. 4,016,218 (Haag).

More recent focus has been directed at liquid phase processes for producing ethylbenzene from benzene and ethylene since liquid phase processes operate at a lower temperature than their vapor phase counterparts and hence tend to result in lower yields of by-products. For example, U.S. Pat. No. 4,891,458 describes the liquid phase synthesis of ethylbenzene with zeolite beta, whereas U.S. Pat. No. 5,334,795 describes the use of MCM-22 in the liquid phase synthesis of ethylbenzene.

Cumene has for many years been produced commercially by the liquid phase alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 describes the use of MCM-22 in the liquid phase alkylation of benzene with propylene.

Other molecular sieves known for use as liquid phase alkylation and transalkylation catalysts include MCM-36 (see U.S. Pat. No. 5,258,565), MCM-49 (see U.S. Pat. No. 5,371,310) and MCM-56 (see U.S. Pat. No. 5,453,554).

Known methods of synthesizing, such as, alkylation or transalkylation catalysts, usually comprise a step of drying them in a deep fixed bed calciner (e.g., having a catalyst height of 1 meter or more) with flowing air or nitrogen.

It is said that one method for modifying the Relative Activity of the final catalyst is by steaming. U.S. Pat. Nos. 4,663,492; 4,594,146; 4,522,929; and 4,429,176 describe conditions for the steam stabilization of zeolite catalysts which can be utilized to steam-stabilize the catalyst. The steam stabilization conditions include contacting the final catalyst with, e.g., 5-100% steam at a temperature of at least about 300° C. (e.g., 300-650° C.) for at least one hour (e.g., 1-200 hours) at a pressure of 101-2,500 kPa. In a more particular embodiment, the final catalyst can be made to undergo steaming with 75-100% steam at 315° C.-500° C. and atmospheric pressure for 2-25 hours. In accordance with the steam stabilization treatment described in the above-mentioned patents, the steaming of the catalyst can take place under conditions sufficient to initially increase the Alpha Value of the catalyst and produce a steamed final catalyst having a peak Alpha Value. If desired, steaming can be continued to subsequently reduce the Alpha Value from the peak Alpha Value to an Alpha Value, which is substantially the same as the Alpha Value of the unsteamed final catalyst.

U.S. Pat. No. 8,222,468 provides a process for conversion of feedstock comprising organic compounds to desirable conversion product at organic compound conversion conditions in the presence of catalyst comprising an acidic, porous crystalline material and having a Proton Density Index of greater than 1.0, for example, from greater than 1.0 to about 2.0, e.g., from about 1.01 to about 1.85. The acidic, porous crystalline material of the catalyst may comprise a porous, crystalline material or molecular sieve having the structure of zeolite Beta, an MWW structure type material, e.g., MCM-22, MCM-36, MCM-49, MCM-56, or a mixture thereof. In this disclosure, a method for producing the catalyst for use is also provided comprising the steps of: (a) providing a first, untreated catalyst, i.e., one not having been treated according to steps (b) and (c) of this method, comprising an acidic, porous crystalline material, said first, untreated catalyst having a first hydration state measured in mmol of protons per gram of catalyst; (b) contacting the first, untreated catalyst of step (a) with water in liquid or gaseous form, at a contact temperature of up to about 500° C., such as from about 1° C. to about 500° C., preferably from about 1° C. to about 99° C., for a contact time of at least about 1 second, preferably from about 1 minute to about 60 minutes, to generate a second catalyst having a second hydration state measured in mmol of protons per gram of catalyst, said second hydration state being greater than said first hydration state, i.e., the product of step (b) has a higher proton density than the step (a) catalyst; and (c) drying the second catalyst resulting from step (b) at a drying temperature of up to about 550° C., preferably from about 20° C. to about 550° C., more preferably from about 100° C. to about 200° C., for a drying time of at least about 0.01 hour, preferably from about 0.1 to about 24 hours, more preferably from about 1 to about 6 hours, to generate the catalyst composition having a third hydration state measured in mmol of protons per gram of catalyst between said first and second hydration states. The step (c) product will have a Proton Density Index of greater than 1.0, for example, from greater than 1.0 to about 2.0, e.g., from about 1.01 to about 1.85.

According to the invention, it has now been found that drying the catalyst, after which being contacted with water, under certain conditions, such as temperature, can result in a difference in selectivity to mono-alkylaromatic compounds of the alkylation or transalkylation catalysts. It has been found that drying the catalysts with a small catalyst deposit height at a low temperature is effective in improving the catalyst selectivity to the mono-alkylaromatic compound. This novel method of the present disclosure provides an efficient and convenient way for treating the aromatic alkylation or transalkylation catalysts to improve catalyst selectivity without substantially deteriorating the catalyst activity.

SUMMARY OF THE INVENTION

In one aspect, the invention resides in a method of treating a catalyst, preferably an alkylation or a transalkylation catalyst, comprising a molecular sieve, the method comprising the steps of:
(a) contacting the untreated catalyst with water to produce a water-contacted catalyst; and
(b) drying the water-contacted catalyst with a drying gas without steam being formed at a temperature of less than about 300° C. to produce a treated catalyst.

Preferably, the drying step can be conducted at a temperature of from about 50° C. to about 250° C. in one embodiment, or from about 100° C. to about 200° C. in another embodiment, or from about 120° C. to about 150° C. or to less than about 150° C. in yet another embodiment.

Preferably, the catalyst deposit height can be less than about 1 meter, or less than about 50 centimeters, or less than about 10 centimeters in one or more embodiments; less than about 8 centimeters in another embodiment, or less than about 5 centimeters in another embodiment; or from about 0.1 to about 10 centimeters in yet another embodiment, or from about 0.5 to about 8 centimeters in yet another embodiment, or from about 1 to about 5 centimeters in yet another embodiment.

Preferably, the residence time of catalyst in the drying step can be from about 1 minute to about 96 hours in one embodiment, or about 30 minutes to 48 hours in another embodiment, or about 1 hour to 36 hours in yet another embodiment, or about 2 hours to about 24 hours in still another embodiment.

Preferably, the water can be deionized water, and preferably, prior to contacting the catalyst with water, the treatment method comprises the step of calcining the catalyst at a temperature of greater than about 300° C.

Preferably, the catalyst comprises a fresh catalyst, an at least partially deactivated catalyst, or combinations thereof. The alkylation or transalkylation catalyst can be a fresh catalyst in one embodiment, for example, a fresh catalyst extrudate. In another embodiment, the catalyst can be an at least partially deactivated catalyst, for example, a catalyst deactivated by coke deposition during an alkylation or transalkylation process.

Preferably, the alkylation or transalkylation catalyst can comprise a MCM-22 family molecular sieve, a faujasite, a mordenite, zeolite beta, or combinations thereof. Preferably, the MCM-22 family molecular sieve is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and combinations thereof.

In another aspect, the present invention resides in a process for producing a mono-alkylaromatic compound, comprising the step of contacting an alkylatable aromatic compound and an alkylating agent with a treated catalyst under alkylation or transalkylation conditions to produce a mono-alkylaromatic compound, wherein the treated catalyst was treated by the method comprising the steps of:

(a) contacting an untreated catalyst with water to produce a water-contacted catalyst, and
(b) drying the water-contacted catalyst with a drying gas with minimal steam being formed at a temperature of less than about 300° C. to produce the treated catalyst.

Preferably, the alkylation or the transalkylation catalyst can comprise a MCM-22 family molecular sieve, a faujasite, a mordenite, zeolite beta, or combinations thereof. Preferably, the MCM-22 family molecular sieve comprises at least one selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30.

Preferably, the contacting step is conducted in at least partial liquid phase; more preferably in the liquid phase.

Preferably, the alkylating agent can include an olefinic group having 1 to 5 carbon atoms, or a poly-alkylaromatic compound.

Preferably, the alkylating agent can be ethylene or propylene and preferably, the alkylatable aromatic compound can be benzene.

Preferably, the alkylation conditions comprises a temperature of from about 50° C. to about 400° C., and a pressure of from about 100 kPa to about 7000 kPa.

It is believed that, but not to be limited by any theory, as the catalyst is deposited in a thin layer during the drying with a drying gas, the water on the catalyst will be volatilized and removed out from the catalyst quickly without forming appreciable amounts of steam and essentially minimal contact of steam with the catalyst bed. Under such conditions. Under such conditions, the water-contacted catalyst will not be kept for a long time in the saturated or almost saturated hydration state under which the catalyst is subjected to steam while drying. It has been surprisingly found that an insufficient or non-steaming status of the catalyst during drying results in a higher catalyst selectivity without substantial deterioration of the catalyst activity. The present invention therefore provides an efficient and convenient way to improve the catalyst selectivity, in particular alkylation or transalkylation catalyst comprising, for example, a MCM-22 family molecular sieve.

DETAILED DESCRIPTION OF THE INVENTION

Figure 1:
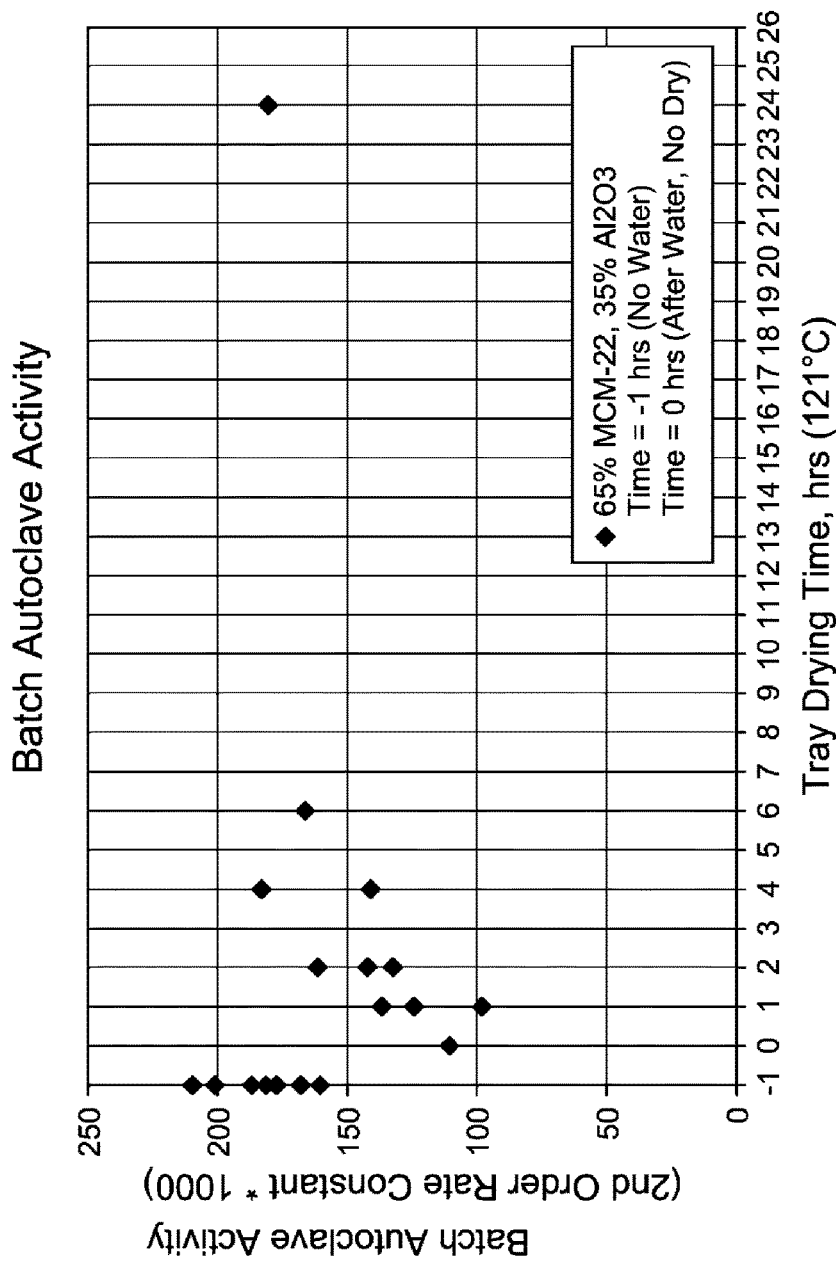
FIG. 1 shows the activity as a 2nd order rate constant for the MCM-22-based catalysts of Examples 5 and Example 6 for the alkylation of benzene with propylene.

The present invention relates to a process for producing a mono-alkylaromatic compound, particularly ethylbenzene or cumene, by the at least partial liquid phase alkylation of an alkylatable aromatic compound with an alkylating agent in the presence of a catalyst (e.g., alkylation or transalkylation catalyst) comprising a molecular sieve. More particularly, the invention is concerned with a process in which the catalyst used in the process is subjected to an catalyst treatment comprising the steps of: (a) contacting the catalyst with water; and (b) drying the water-contacted alkylation catalysts at a temperature of less than about 300° C. with a catalyst deposit height of less than about 10 centimeters so as to improve the catalyst selectivity to the desired mono-alkylaromatic compound, without substantially deteriorating the catalyst activity.

The term "alkylatable aromatic compound" as used herein means an aromatic compound that may receive an alkyl group. One non-limiting example of an alkylatable aromatic compound is benzene.

The term "alkylating agent" as used herein means a compound which may donate an alkyl group to an alkylatable aromatic compound. Non-limiting examples of an alkylating agent are ethylene, propylene, and butylene. Another non-limiting example is any poly-alkylaromatic compound that is capable of donating an alkyl group to an alkylatable aromatic compound.

The term "aromatic" as used herein in reference to the alkylatable aromatic compounds which are useful herein is to be understood in accordance with its art-recognized scope which includes substituted and unsubstituted mono- and polynuclear compounds. Compounds of an aromatic character which possess a heteroatom (e.g., N or S) are also useful provided they do not act as catalyst poisons, as defined below, under the reaction conditions selected.

The term "liquid phase" as used herein, means a mixture having at least 1 wt. % liquid phase, optionally at least 5 wt. % liquid phase, at a given temperature, pressure, and composition.

The term "at least partially deactivated", or "deactivated", as used herein, means alkylation or transalkylation catalyst activity is decreased by an amount of at least 1% deactivated compared to initial alkylation catalyst activity.

The term "framework type" as used herein has the meaning described in the "Atlas of Zeolite Framework Types," by Ch. Baerlocher, W. M. Meier and D. H. Olson (Elsevier, 5th Ed., 2001).

The term "MCM-22 family material" (or "MCM-22 family molecular sieve"), as used herein, can include:

(i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier and D. H. Olson (Elsevier, 5th Ed., 2001);

(ii) molecular sieves made from a common second degree building block, a 2-dimensional tiling of such MWW framework type unit cells, forming a "monolayer of one unit cell thickness," preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system.

The term "mono-alkylaromatic compound" means an aromatic compound that has only one alkyl substituent. Non-limiting examples of mono-alkylaromatic compounds are ethylbenzene, iso-propylbenzene (cumene) and sec-butylbenzene.

The term "poly-alkylaromatic compound" as used herein means an aromatic compound that has more than one alkyl substituent. A non-limiting example of a poly-alkylaromatic compound is poly-alkylated benzene, e.g., di-ethylbenzene, tri-ethylbenzene, di-isopropylbenzene, and tri-isopropylbenzene.

Substituted alkylatable aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable alkylatable aromatic hydrocarbons include benzene, naphthalene, anthracene, naphthacene, perylene, coronene, and phenanthrene, with benzene being preferred.

Generally the alkyl groups, which can be present as substituents on the aromatic compound, contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalene; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes make in such instances may be less than about 500 ppm.

Reformate containing substantial quantities of benzene, toluene and/or xylene constitutes a particularly useful feed for the alkylation process of this invention.

The alkylating agents, which are useful in the process of this invention, generally include any aliphatic or aromatic organic compound having one or more available alkylating olefinic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mol. % |
| --- | --- | --- |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-butane | 3.3 | 2.6 |
| Butenes | 22.1 | 18.32 |
| Pentanes | 0.7 | 0.4 |

Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes.

The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions can include at least one of the following: a temperature of from about 50° C. and about 400° C., preferably from about 70° C. to about 300° C., a pressure of from about 100 kPa to about 7000 kPa, preferably from about 300 kPa to about 5000 kPa, a molar ratio of alkylatable aromatic compound to alkylating agent of from about 0.1:1 to about 50:1, preferably from about 0.5:1 to 10:1, and a feed weight hourly space velocity (WHSV) of between about 0.1 and 100 hr$^{-1}$, preferably from about 0.5 to 50 hr$^{-1}$.

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

When benzene is alkylated with ethylene to produce ethylbenzene, the alkylation reaction may be carried out in the liquid phase. Suitable liquid phase conditions include a temperature between about 150° C. and 300° C., preferably between about 200° C. and 260° C., a pressure up to about 20000 kPa, preferably from about 200 kPa to about 5600 kPa, a WHSV of from about 0.1 hr$^{-4}$ to about 50 hr$^{-4}$, preferably from about 1 hr$^{-1}$ and about 10 hr$^{-1}$ based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the reaction may also take place under liquid phase conditions including a temperature of up to about 250° C., preferably from about 10° C. to about 200° C.; a pressure up to about 25000 kPa, preferably from about 100 kPa to about 3000 kPa; and a WHSV of from about 1 hr$^{-4}$ to about 250 hr$^{-4}$, preferably from 5 hr$^{-1}$ to 50 hr$^{-1}$, preferably from about 5 hr$^{-1}$ to about 10 hr$^{-1}$ based on the ethylene feed.

In some embodiments, the alkylation catalyst comprises a MCM-22 family molecular sieve. The MCM-22 family molecular sieves have been found to be useful in alkylation processes for production of mono-alkylaromatic compounds. Examples of MCM-22 family molecular sieve are MCM-22 (described in U.S. Pat. No. 4,954,325), MCM-36 (described in U.S. Pat. No. 5,250,277), MCM-49 (described in U.S. Pat. No. 5,236,575), MCM-56 (described in U.S. Pat. No. 5,362,697), PSH-3 (described in U.S. Pat. No. 4,439,325), ITQ-1 (described in U.S. Pat. No. 6,077,498), ITQ-2 (described in International Patent Publication No. WO97/17290), ITQ-30 (described in International Patent Publication No. WO2005118476), SSZ-25 (described in U.S. Pat. No. 4,826,667), a EMM-10 family molecular sieve (described or characterized in U.S. Pat. Nos. 7,959,899 and 8,110,176; and U.S. Patent Application Publication No. 2008/0045768), such as EMM-10, EMM-12, EMM-13, ERB-1 (described in European Patent No. 0293032), UZM-8 (described in U.S. Pat. No. 6,756,030) and UZM-8HS (described in U.S. Pat. No. 7,713,513). More preferred MCM-22 family molecular sieve can comprise MCM-22, MCM-36, MCM-49, and MCM-56. In other embodiments, the alkylation catalyst can comprise faujasite, mordenite, and zeolite beta (described in detail in U.S. Pat. No. 3,308,069).

The molecular sieve can be combined in conventional manner with an oxide binder, such as alumina, such that the final alkylation catalyst contains between 2 and 80 wt % sieve.

In some embodiments, the catalyst that can be treated by the method according to the invention can be a fresh catalyst, for example, made by any known method, or an at least partially deactivated catalyst, for example, deactivated in a previous alkylation reaction, or can be a regenerated catalyst using any known methods in the art. The term "fresh" as used herein means the catalyst has not been used in a catalytic reaction after being manufactured.

The catalyst can be treated with any known methods prior to being contacted with water and then dried; for example, the catalyst can be calcined at a temperature of greater than about 300° C.

In some embodiments, the catalyst can be contacted with deionized liquid water, and then dried at a temperature of less than about 300° C.; for example, from about 50° C. to about 250° C., or less than about 200° C.; for example, from about 50° C. to about 180° C., or from about 100° C. to about 160° C., or from about 120° C. to about 150° C., or less than 150° C.; for example, from about 50° C. to less than 150° C., or from about 120° C. to less than about 150° C.

In some embodiments, the catalyst during the drying can be deposited in a catalyst deposit height of less than about 1 meter. In other embodiments, less than about 50 centimeters, or less than about 25 centimeters, or less than about 20 centimeters, or less than about 10 centimeters; for example, about 9 centimeters or less, about 8 centimeters or less, about 7 centimeters or less, about 6 centimeters or less, about 5 centimeters or less, about 4 centimeters or less, or about 3 centimeters or less, about 2 centimeters or less; about 1 centimeter or less. In some embodiments, the catalyst can be deposited in a catalyst deposit height of about 0.1 centimeter or more, for example, about 0.2 centimeter or more, about 0.1 centimeter or more, about 0.2 centimeter or more, about 0.3 centimeter or more, about 0.4 centimeter or more, about 0.5 centimeter or more, about 0.6 centimeter or more, about 0.7 centimeter or more, about 0.8 centimeter or more, about 0.9 centimeter or more. In some embodiments, the catalyst can be deposited in a catalyst deposit height ranging from any two values as above described so long as the low limit value is less than the upper limit value; for example, from about 0.1 to about 10 centimeters, or from about 0.5 to about 8 centimeters, or from about 1 to about 5 centimeters. The term "catalyst deposit height" as used herein means the smallest thickness, when deposited, among all dimensions of the deposited catalyst.

The drying of catalyst can be conducted with flowing drying gas. The drying gas can flow at any direction. In one embodiment, the drying gas can flow along the direction of the catalyst deposit height through the catalyst, or can flow along the direction vertical to the catalyst deposit height. The drying gas can be any gas that is not reactive under the drying conditions, such as air, nitrogen, oxygen, or any other suitable gas. The temperature of drying gas can be less than 300° C., less than about 200° C.; for example, from about 50° C. to about 180° C., or from about 100° C. to about 160° C., or from about 120° C. to about 150° C.

The dryer can be a fixed or moving shallow dryer. Non-limiting examples of such dryers include a shallow moving bed dryer or a shallow moving bed tray. The term "shallow" as used herein means that the depth of the dryer is less than about 1 meter, or less than about 50 centimeters, or less than about 20 centimeters, or less than about 25 centimeters, or less than about 10 centimeters, for example, about 8 centimeters or less, about 5 centimeters or less, or about 3 centimeters or less.

The drying can be conducted for a period of greater than about 1 minute; for example, from 1 minute to about 96 hours in one embodiment, or about 30 minutes to 48 hours in another embodiment, or about 1 hour to 36 hours in still another embodiment, or about 2 hours to about 24 hours in yet another embodiment.

As the alkylation process of the invention proceeds, the alkylation catalyst will gradually lose its alkylation activity, such that the reaction temperature required achieves a given performance parameter; for example, conversion of the alkylating agent will increase. According to the invention, when the alkylation catalyst activity has decreased by some predetermined amount, typically 5% to 90% and, more preferably 10% to 50%, compared to the initial alkylation catalyst activity, the deactivated catalyst can be subjected to the novel treatment procedure of the present invention.

In some embodiments, the deactivated catalyst can be regenerated using any known method and then treated with the procedure of the present invention.

The alkylation process of the invention is particularly intended to produce mono-alkylaromatic compounds, such as ethylbenzene and cumene, but the alkylation step will normally produce some poly-alkylaromatic compounds. Thus. the process preferably includes the further steps of separating the poly-alkylaromatic compounds from the alkylation effluent and reacting them with additional aromatic feed in a transalkylation reactor over a suitable transalkylation catalyst. The transalkylation catalyst is preferably a molecular sieve which is selective to the production of the desired mono-alkylaromatic compound and can, for example, employ the same molecular sieve as the alkylation catalyst, preferably the MCM-22 family molecular sieves, such as MCM-22, MCM-49, MCM-56, and zeolite beta. In addition, the transalkylation catalyst may be faujasite and mordenite, such as TEA-mordenite.

The transalkylation reaction of the invention is conducted in the liquid phase under suitable conditions such that the polyalkylated aromatics react with the additional aromatic feed to produce additional monoalkylated product. Suitable transalkylation conditions include a temperature of 100° C. to 260° C., a pressure of about 200 kPa to about 600 kPa, a weight hourly space velocity of 1 to 10 on total feed, and aromatic/poly-alkylaromatic compound weight ratio 1:1 to 6:1.

When the polyalkylated aromatics are polyethylbenzenes and are reacted with benzene to produce ethylbenzene, the transalkylation conditions preferably include a temperature of from about 220° C. to about 260° C., a pressure of from about 300 kPa to about 400 kPa, weight hourly space velocity of 2 to 6 on total feed and benzene/PEB weight ratio 2:1 to 6:1.

When the polyalkylated aromatics are polypropylbenzenes and are reacted with benzene to produce cumene, the transalkylation conditions preferably include a temperature of from about 100° C. to about 200° C., a pressure of from about 300 kPa to about 400 kPa, a weight hourly space velocity of 1 to 10 on total feed and benzene/PIPB weight ratio 1:1 to 6:1.

As the transalkylation catalyst becomes deactivated, it may be subjected to the same treatment as described herein in relation to the alkylation catalyst. Accordingly, the present invention also resides in a process for producing a mono-alkylaromatic compound, comprising: (i) treating a transalkylation catalyst comprising a molecular sieve comprising the steps of: (a) contacting the transalkylation catalyst with water, for example, deionized water, and (b) drying the water-contacted transalkylation catalyst at a temperature of less than about 300° C. with a catalyst deposit height of less than about 10 centimeters; and (ii) contacting an alkylatable aromatic compound and a poly-alkylaromatic compound with the treated transalkylation catalyst of step (i) under transalkylation conditions to produce a mono-alkylaromatic compound.

The treatment method of the present disclosure is found to be effective in improving catalyst selectivity without substantially deteriorating the catalyst activity.

The invention will now be more particularly described with reference to the following Examples. In the Examples, the activity and selectivity of a catalyst were measured based on benzene alkylation with propylene. Catalyst activity was calculated using the intrinsic second order rate constant for the formation of cumene under the reaction conditions (temperature 130° C. and pressure 2170 kPa). Reaction rate-constants were calculated using methods known to those skilled in the art. See "Principles and Practice of Heterogeneous Catalyst", J. M. Thomas, W. J. Thomas, VCH, 1st Edition, 1997, the disclosure of which is incorporated herein by reference. Catalyst selectivity was calculated using the weight ratio of di-isopropyl benzenes produced to cumene produced (DIPB/IPB) and tri-isopropyl benzenes produced to cumene produced (Tri-IPB/IPB) under the reaction conditions (temperature 130° C. and pressure 2758 kPa).

Example 1

A catalyst was prepared in a deep fixed bed calciner. The catalyst comprised 80 wt. % MCM-49 (as described in U.S.

Pat. No. 5,236,575) and 20 wt. % Al$_2$O$_3$. One-half gram of the catalyst was charged to an isothermal well-mixed Parr autoclave reactor along with a mixture comprising benzene (156 g) and propylene (28 g). The reaction was carried out at 130° C. and 2758 kPa for 3 hours. The catalyst performance was assessed and shown in Tables 1 to 3.

Example 2

The catalyst prepared in Example 1 was washed with deionized water after air calcination, and dried at 400° C. with flowing air or nitrogen in a deep bed calciner with a catalyst deposit height of about 10 meters for 16 hours. One-half gram of the treated catalyst was evaluated for benzene alkylation with propylene according to the procedure described in Example 1. The catalyst performance was assessed and shown in Tables 1 to 3.

Example 3

The catalyst prepared in Example 1 was washed with deionized water after air calcination, and dried at 150° C. in a continuous shallow moving bed dryer with a catalyst deposit height of about 2.5 centimeters for 16 hours. One-half gram of the treated catalyst was evaluated for benzene alkylation with propylene according to the procedure described in Example 1. The catalyst performance was assessed and shown in Tables 1 to 3.

Example 4

The catalyst prepared in Example 1 was washed with deionized water after air calcination, and dried at 121° C. in a shallow bed tray having a catalyst deposit height of about 2.5 centimeters for 16 hours. One-half gram of the treated catalyst was evaluated for benzene alkylation with propylene according to the procedure described in Example 1.

Example 5

Figure 2:
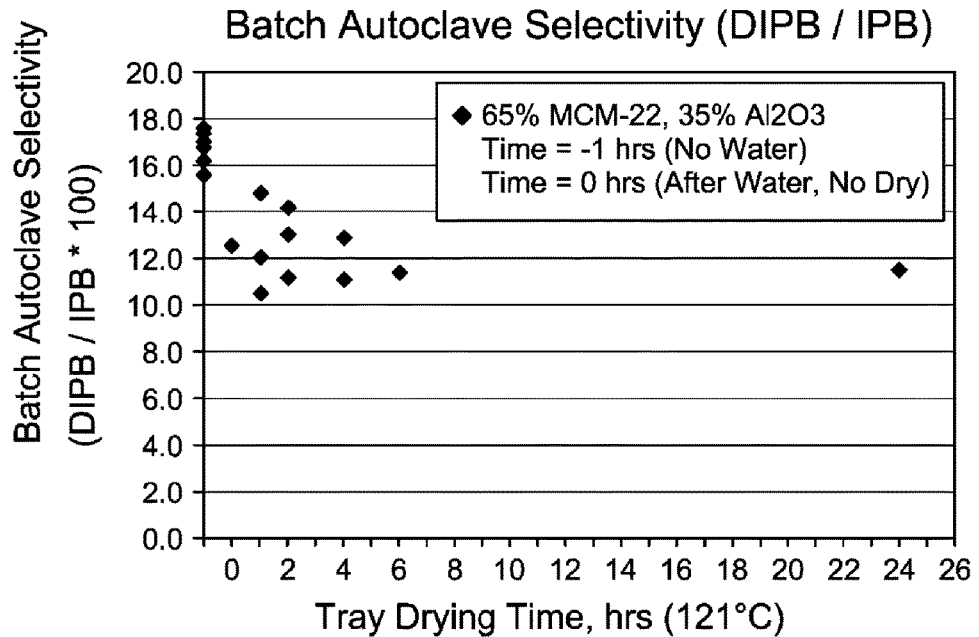
FIG. 2 shows the DIPB/IPB selectivity for the MCM-22-based catalysts of Examples 5 and Example 6 for the alkylation of benzene with propylene.
Figure 3:
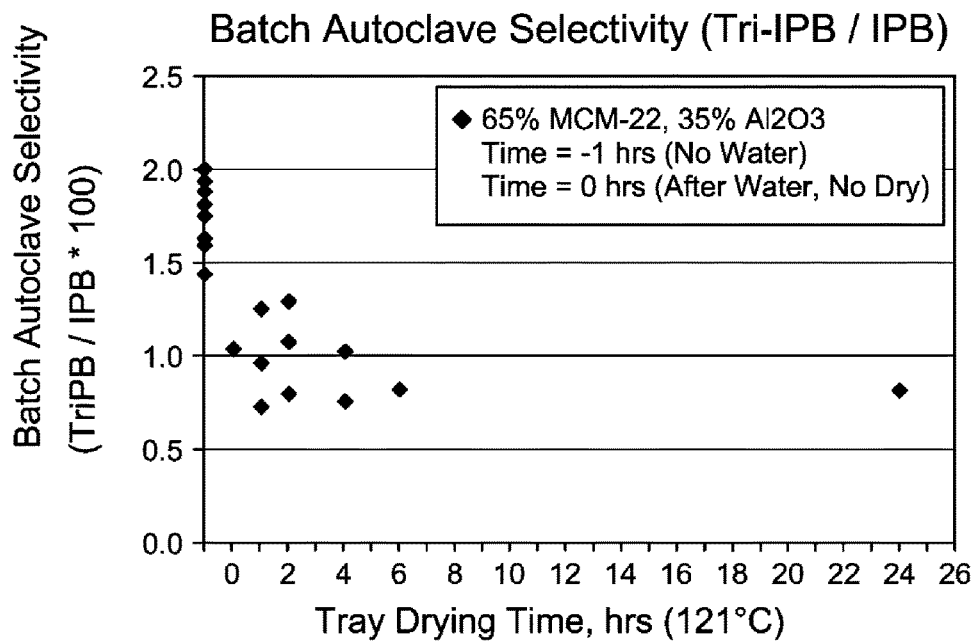
FIG. 3 shows the Tri-IPB selectivity for the MCM-22-based catalysts of Examples 5 and Example 6 for the alkylation of benzene with propylene.

A catalyst was prepared in a deep fixed bed calciner. The catalyst comprised 65 wt. % MCM-22 (as described in U.S. Pat. No. 4,954,325) and 35 wt. % Al$_2$O$_3$. One-half gram of the catalyst was charged to an isothermal well-mixed Parr autoclave reactor along with a mixture comprising benzene (156 g) and propylene (28 g). The reaction was carried out at 130° C. and 2170 kPa for 4 hours. The catalyst performance was assessed and shown in FIGS. 1 to 3.

Example 6

The catalyst prepared in Example 5 was washed with deionized water after air calcination, and dried at 121° C. in a shallow bed tray having a catalyst deposit height of about 2.5 centimeters for 0 to 24 hours. One-half gram of the treated catalyst was evaluated for benzene alkylation with propylene according to the procedure described in Example 5. The catalyst performance was assessed and shown in FIGS. 1 to 3.

TABLE 1

Boxplot results of 2nd order rate constant * 1000

|  | Example 1 | Example 2 | Example 3 | Example 4 |
|---|---|---|---|---|
| Outliers | 6 | 0 | 1 | 0 |
| Count | 172 | 95 | 4 | 7 |
| Median | 329 | 302 | 312 | 280 |
| Average | 323 | 303 | 331 | 264 |

TABLE 1-continued

Boxplot results of 2nd order rate constant * 1000

|  | Example 1 | Example 2 | Example 3 | Example 4 |
|---|---|---|---|---|
| Std. Dev. | 46 | 37 | 52 | 37 |
| P10 | 264 | 258 | 298298.1 | 226 |
| P90 | 381 | 354 | 380 | 302 |

TABLE 2

Boxplot results of selectivity: DIPB/IPB

|  | Example 1 | Example 2 | Example 3 | Example 4 |
|---|---|---|---|---|
| Outliers | 9 | 9 | 0 | 1 |
| Count | 172 | 95 | 4 | 7 |
| Median | 18.6 | 16.4 | 15.0 | 12.9 |
| Average | 18.5 | 16.5 | 15.0 | 13.1 |
| Std. Dev. | 1.17 | 1.60 | 0.13 | 0.59 |
| P10 | 17.3 | 15.0 | 14.8 | 12.7 |
| P90 | 19.8 | 18.3 | 15.1 | 13.7 |

TABLE 3

Boxplot results of selectivity: Tri-IPB/IPB

|  | Example 1 | Example 2 | Example 3 | Example 4 |
|---|---|---|---|---|
| Outliers | 14 | 8 | 0 | 1 |
| Count | 172 | 95 | 4 | 7 |
| Median | 2.24 | 1.68 | 1.40 | 1.15 |
| Average | 2.10 | 1.72 | 1.41 | 1.17 |
| Std. Dev. | 3.2 | 0.35 | 0.24 | 0.09 |
| P10 | 1.74 | 1.3 | 1.39 | 1.10 |
| P90 | 2.51 | 2.14 | 1.43 | 1.26 |

Example 7

A catalyst was prepared in a deep fixed bed calciner. The catalyst comprised 80 wt. % USY (as described in U.S. Pat. Nos. 3,293,192 and 3,449,070, and is a form of faujasite) and 20 wt. % Al$_2$O$_3$. One-half gram of the catalyst was charged to an isothermal well-mixed Parr autoclave reactor along with a mixture comprising benzene (156 g) and propylene (28 g). The reaction was carried out at 130° C. and 2758 kPa for 3 hours. The catalyst performance was assessed and shown in Table 4.

Example 8

The catalyst prepared in Example 7 was washed with deionized water after air calcination, and dried at 121° C. in a shallow bed tray having a catalyst deposit height of about 2.5 centimeters for 8 hours. One-half gram of the treated catalyst was evaluated for benzene alkylation with propylene according to the procedure described in Example 7. The catalyst performance was assessed and shown in Table 4.

Example 9

A catalyst was prepared in a deep fixed bed calciner. The catalyst comprised 80 wt. % zeolite beta (as described in U.S. Pat. No. 3,308,069) and 20 wt. % Al$_2$O$_3$. One-half gram of the catalyst was charged to an isothermal well-mixed Parr autoclave reactor along with a mixture comprising benzene (156 g) and propylene (28 g). The reaction was carried out at 130° C. and 2758 kPa for 3 hours. The catalyst performance was assessed and shown in Table 4.

Example 10

The catalyst prepared in Example 9 was washed with deionized water after air calcination, and dried at 121° C. in a shallow bed tray having a catalyst deposit height of about 2.5 centimeters for 8 hours. One-half gram of the treated catalyst was evaluated for benzene alkylation with propylene according to the procedure described in Example 9. The catalyst performance was assessed and shown in Table 4.

TABLE 4

| | Cumene Activity ($2^{nd}$ Order Rate Constant) Normalized to Comparative | DIPB/IPB Selectivity Normalized to Comparative | Tri-IPB/IPB Selectivity Normalized to Comparative |
|---|---|---|---|
| Example 7 (Comparative) | 100% | 100% | 100% |
| Example 8 | 200% | 36% | 58% |
| Example 9 (Comparative) | 100% | 100% | 100% |
| Example 10 | 84% | 130% | 36% |

Example 11

A catalyst was prepared in a deep fixed bed calciner. The catalyst comprised 60 wt. % MCM-56 (as described in U.S. Pat. No. 5,362,697) and 40 wt. % $Al_2O_3$. One-half gram of the catalyst was charged to an isothermal well-mixed Parr autoclave reactor along with a mixture comprising benzene (156 g) and propylene (28 g). The reaction was carried out at 130° C. and 2758 kPa for 3 hours. The catalyst performance was assessed and shown in Table 5.

Examples 12 to 16

The catalyst prepared in Example 11 was washed with deionized water after air calcination, and dried at 121° C. in a shallow bed tray having a catalyst deposit height of about 2.5 centimeters for various time periods from 1 to 24 hours. One-half gram of the treated catalyst was evaluated for benzene alkylation with propylene according to the procedure described in Example 11. The catalyst performance was assessed and shown in Table 5.

TABLE 5

| | Drying Time (Hours) | Average Cumene Activity* Normalized to Comparative | Average DIPB/IPB Selectivity Normalized to Comparative | Average Tri-IPB/IPB Selectivity Normalized to Comparative |
|---|---|---|---|---|
| Example 11 (Comparative) | None | 100% | 100% | 100% |
| Example 12 | 1 | 56% | 61% | 45% |
| Example 13 | 2 | 68% | 72% | 60% |
| Example 14 | 4 | 66% | 67% | 50% |
| Example 15 | 6 | 82% | 78% | 65% |
| Example 16 | 24 | 93% | 72% | 55% |

*Average $2^{nd}$ Order Rate Constant

As can be seen in Tables 1 to 5, the catalyst treatment of the present invention in which the catalyst was dried with a small catalyst deposit height (Examples 3, 4, 6, 8, 10 and 12 to 16), is more effective at improving the catalyst DIPB/IPB and Tri-IPB/IPB selectivities for a process of making cumene, and the catalyst activity in a process for making cumene was comparable to those in which the catalyst was dried in deep fixed bed calciner having a catalyst deposit height of more than 1 meter (Examples 2, 5, 7, 9 and 11).

Example 17

A catalyst was prepared in a deep fixed bed calciner. The catalyst comprised 60 wt. % MCM-56 (as described in U.S. Pat. No. 5,362,697) and 40 wt. % $Al_2O_3$. One-half gram of the catalyst was charged to an isothermal well-mixed Parr autoclave reactor along with a mixture comprising benzene (156 g) and propylene (28 g). The reaction was carried out at 130° C. and 2758 kPa for 3 hours. The catalyst performance was assessed and shown in Table 6.

Examples 18 to 21

The catalyst prepared in Example 17 was washed with deionized water after air calcination, and dried at temperatures from 121° C. to 400° C. in a simulated deep bed dryer having a catalyst deposit height of about 20 centimeters for 24 hours. One-half gram of the treated catalyst was evaluated for benzene alkylation with propylene according to the procedure described in Example 17. The catalyst performance was assessed and shown in Table 6.

TABLE 6

| | Example | | | | |
|---|---|---|---|---|---|
| | 17 (Comparative) | 18 | 19 | 20 | 21 |
| Drying Temperature (° C.) | None | 121° C. | 177° C. | 260° C. | 400° C. |
| Average Cumene Activity* Normalized to Comparative | 100% | 76% | 89% | 92% | 76% |
| Average DIPB/IPB Selectivity Normalized to Comparative | 100% | 68% | 63% | 67% | 91% |
| Average Tri-IPB/IPB Selectivity Normalized to Comparative | 100% | 51% | 43% | 47% | 94% |

*Average $2^{nd}$ Order Rate Constant

As can be seen in Table 6, the catalyst treatment of the present invention in which the catalyst was dried at temperatures from 121° C. to 400° C. in a simulated deep bed dryer having a catalyst deposit height of about 30 centimeters for 24 hours (Examples 18 to 21), the average catalyst activity and DIPB/IPB and Tri-IPB/IPB selectivities increases with increasing temperature in a process for making cumene.

Example 22

A catalyst was prepared in a deep fixed bed calciner. The catalyst comprised 60 wt. % MCM-56 (as described in U.S. Pat. No. 5,362,697) and 40 wt. % $Al_2O_3$. One-half gram of the catalyst was charged to an isothermal well-mixed Parr autoclave reactor along with a mixture comprising benzene (156 g) and propylene (28 g). The reaction was carried out at 130° C. and 2170 kPa for 4 hours. The catalyst performance was assessed and shown in Table 7.

Example 23 TO 26

The catalyst prepared in Example 22 was washed with deionized water after air calcination, and dried at 167° C. to 171° C. in a shallow bed vacuum oven under vacuum conditions of 27 inches (69 centimeters) of mercury having a catalyst deposit height of about 2.5 centimeters for various time periods from 3 to 24 hours. One-half gram of the treated catalyst was evaluated for benzene alkylation with propylene according to the procedure described in Example 22. The catalyst performance was assessed and shown in Table 7.

TABLE 7

| | Example | | | | |
|---|---|---|---|---|---|
| | 22 (Comparative) | 23 | 24 | 25 | 26 |
| Drying Time (hours) | None | 3 | 5 | 6 | 24 |
| Average Cumene Activity* Normalized to Comparative | 100% | 90% | 92% | 73% | 73% |
| Average DIPB/IPB Selectivity Normalized to Comparative | 100% | 160% | 163% | 165% | 168% |
| Average Tri-IPB/IPB Selectivity Normalized to Comparative | 100% | 55% | 56% | 57% | 61% |

*Average 2$^{nd}$ Order Rate Constant

As can be seen in Table 7, the catalyst treatment of the present invention in which the catalyst was dried at 167° C. to 171° C. in a shallow bed dryer under vacuum conditions (at 27 inches of mercury) at various time periods from 3 to 24 hours (Examples 23 to 26), the average catalyst activity and DIPB/IPB selectivity decreased with increasing drying time in a process for making cumene; however, the average Tri-IPB/IPB selectivity increased with increasing drying time in a process for making cumene.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

What is claimed is:

1. A process for producing an alkylated aromatic compound, comprising the step of contacting an alkylatable aromatic compound and an alkylating agent with a treated catalyst under alkylation or transalkylation conditions to produce the alkylated aromatic compound, wherein the treated catalyst was treated by the method comprising the steps of:
    (a) contacting an untreated catalyst with water to produce a water-contacted catalyst, and
    (b) drying the water-contacted catalyst with a drying gas at a temperature of less than about 300° C. to produce a treated catalyst; and
    wherein the water-contacted catalyst of drying step (b) is dried at a deposit height of less than about 10 centimeters.

2. The process of claim 1, wherein the drying gas flows along the direction of the catalyst deposit height through the water-contacted catalyst.

3. The process of claim 1, wherein the drying gas flows in a direction vertical to the catalyst deposit height.

4. The process of claim 1, wherein the drying step (b) is conducted at a temperature of from about 50° C. to about 250° C.

5. The method of claim 1, wherein drying step (b) is conducted for a period of from about 1 minute to about 96 hours.

6. The process of claim 1, wherein the catalyst comprises a fresh catalyst, and at least partially deactivated catalyst, or combinations thereof.

7. The process of claim 1, wherein the water is deionized water.

8. The process of claim 1, further comprising the step of, prior to contacting the catalyst with water in step (a), calcining the catalyst at a temperature of greater than about 300° C.

9. The process of claim 1, wherein the molecular sieve is selected from the group consisting of a MCM-22 family molecular sieve, faujasite, mordenite, or zeolite-beta, and combinations thereof.

10. The process of claim 9, wherein the MCM-22 family molecular sieve is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and combinations thereof.

11. The process of claim 1, wherein the contacting step is conducted under at least partial liquid phase conditions.

12. The process of claim 1, wherein the alkylating agent is an alkylating olefinic group having 1 to 5 carbon atoms or a poly-alkylaromatic compound.

13. The process of claim 1, wherein the alkylating agent is ethylene or propylene.

14. The process of claim 1, wherein the alkylatable aromatic compound is benzene.

15. The process of claim 1, wherein the alkylation or transalkylation conditions comprises a temperature of from 50° C. to about 400° C., and a pressure of from about 100 kPa to about 7000 kPa.

16. A method of treating a catalyst comprising a molecular sieve, comprising the steps of:
(a) contacting an untreated catalyst with water to produce a water contacted catalyst; and
(b) drying the water-contacted catalyst with a drying gas at a temperature of less than about 300° C. to produce a treated catalyst; and
wherein the water-contacted catalyst of drying step (b) is dried at a deposit height of less than about 10 centimeters.

17. The method of claim 16, wherein drying step (b) is conducted at a temperature of from about 50° C. to about 250° C.

18. The method of claim 16, wherein drying step (b) is conducted for a period of from about 1 minute to about 96 hours.

19. The method of claim 16, wherein the untreated catalyst comprises a fresh catalyst, an at least partially deactivated catalyst, or combinations thereof.

20. The method of claim 16, wherein the water is deionized water.

21. The method of claim 16, further comprising the step of, prior to contacting step (a), calcining the catalyst at a temperature of greater than about 300° C.

22. The method of claim 16, wherein the molecular sieve is selected from the group consisting of a MCM-22 family molecular sieve, faujasite, mordenite, zeolite-beta, and combinations thereof.

23. The method of claim 22, wherein the MCM-22 family molecular sieve is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and combinations thereof.

* * * * *